(12) United States Patent
Williams et al.

(10) Patent No.: US 11,931,538 B2
(45) Date of Patent: *Mar. 19, 2024

(54) THERAPEUTIC DELIVERY DEVICE

(71) Applicant: UNIVERSITY OF UTAH RESEARCH FOUNDATION, Salt Lake City, UT (US)

(72) Inventors: Dustin Williams, Farmington, UT (US); Nicholas Ashton, Holladay, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 696 days.

This patent is subject to a terminal disclaimer.

(21) Appl. No.: 16/994,575

(22) Filed: Aug. 15, 2020

(65) Prior Publication Data

US 2020/0376250 A1    Dec. 3, 2020

Related U.S. Application Data

(63) Continuation of application No. 16/047,917, filed on Jul. 27, 2018, now Pat. No. 10,744,313.
(Continued)

(51) Int. Cl.
*A61M 39/02* (2006.01)
*A61M 31/00* (2006.01)
*A61M 39/10* (2006.01)

(52) U.S. Cl.
CPC ...... *A61M 39/0247* (2013.01); *A61M 31/002* (2013.01); *A61M 39/1011* (2013.01);
(Continued)

(58) Field of Classification Search
CPC ............ A61M 31/002; A61M 39/1011; A61M 2039/0276; A61M 2205/04;
(Continued)

(56) References Cited

U.S. PATENT DOCUMENTS 4,300,557 A * 11/1981 Refojo .................. A61F 9/0017
424/424
4,417,576 A * 11/1983 Baran ............... A61M 16/0481
604/101.02

(Continued)

*Primary Examiner* — Quynh-Nhu H. Vu
(74) *Attorney, Agent, or Firm* — PARTNERS LAW GROUP; Steve Hassid

(57) ABSTRACT

A therapeutic delivery device that provides a controlled release of high doses of a therapeutic agent in a local area, sustains the high dose controlled release with a percutaneous port for refilling the device, and is versatile for use with multiple types of therapeutic agents and/or implant systems. A rate determining/controlled release membrane is used to decrease the molecular mobility of the therapeutic compounds thereby controlling the therapeutic release profile. The therapeutic delivery device includes a body defining an internal reservoir for receiving a therapeutic agent and including a first membrane for providing a controlled release of the therapeutic agent to the surgical site, a port in fluid communication with the reservoir, a sleeve configured to encapsulate the body, and a rigid housing configured to support the body and a portion of the sleeve, the rigid
(Continued)

housing configured to release the body and the sleeve after the body and the sleeve are anchored position relative to the surgical site.

14 Claims, 20 Drawing Sheets

Related U.S. Application Data

(60) Provisional application No. 62/537,596, filed on Jul. 27, 2017.

(52) U.S. Cl.
CPC ............ *A61M 2039/0205* (2013.01); *A61M 2039/0276* (2013.01); *A61M 2039/0288* (2013.01); *A61M 2205/0205* (2013.01); *A61M 2205/04* (2013.01); *A61M 2209/045* (2013.01); *A61M 2210/02* (2013.01)

(58) Field of Classification Search
CPC ........ A61M 2209/045; A61M 2210/02; A61M 2039/0205; A61M 2039/0288
See application file for complete search history.

(56) References Cited

U.S. PATENT DOCUMENTS

| | | | | |
|---|---|---|---|---|
| 4,576,604 | A * | 3/1986 | Guittard | A61K 9/0004 424/431 |
| 6,001,386 | A * | 12/1999 | Ashton | A61P 27/02 623/6.11 |
| 6,004,582 | A * | 12/1999 | Faour | A61P 11/00 424/475 |
| 6,375,972 | B1 * | 4/2002 | Guo | A61K 9/5089 424/422 |
| 6,471,689 | B1 * | 10/2002 | Joseph | A61M 5/1723 424/424 |
| 7,090,668 | B1 * | 8/2006 | U | A61K 9/0024 604/892.1 |
| 9,492,315 | B2 * | 11/2016 | de Juan, Jr. | A61P 27/02 |
| 9,795,468 | B2 * | 10/2017 | Mujwid | A61F 2/0045 |
| 10,092,507 | B2 * | 10/2018 | Hennemann | A61K 38/14 |
| 2010/0114066 | A1 * | 5/2010 | Makower | G03G 5/14726 604/514 |
| 2020/0376251 | A1 * | 12/2020 | Williams | A61M 39/1011 |
| 2021/0031016 | A1 * | 2/2021 | Williams | A61M 39/0247 |
| 2021/0031017 | A1 * | 2/2021 | Williams | A61M 39/1011 |

* cited by examiner

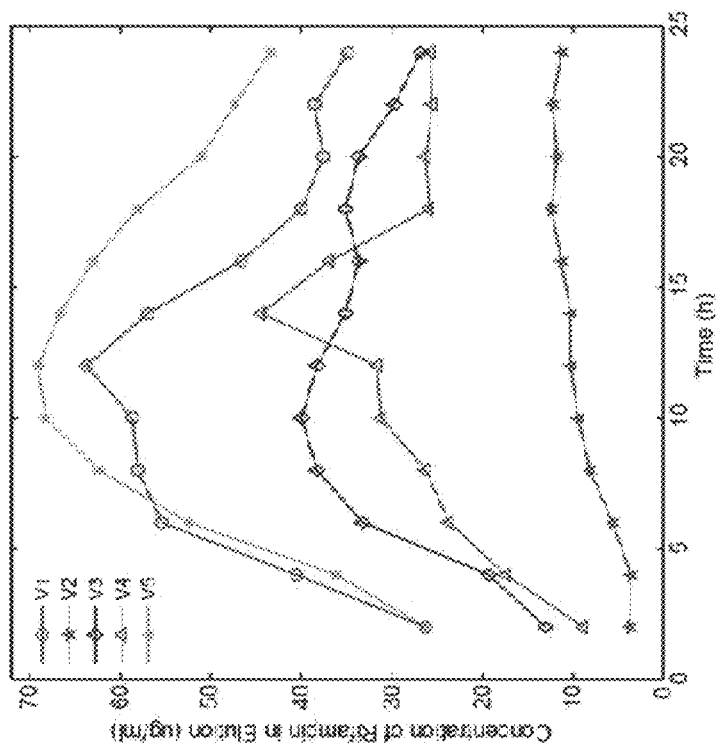
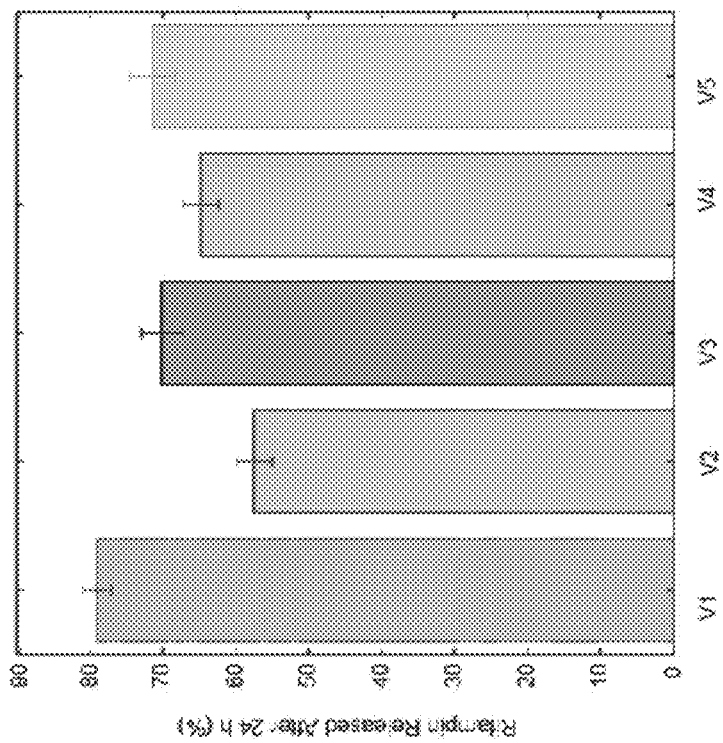
FIG. 14B
FIG. 14A

THERAPEUTIC DELIVERY DEVICE

CROSS-REFERENCE TO RELATED APPLICATIONS

This application is a continuation application of and claims the benefit of and priority to U.S. patent application Ser. No. 16/047,917 filed on Jul. 27, 2018, which issued as U.S. Pat. No. 10,744,313 on Aug. 18, 2020, which claim the benefit of and priority to U.S. Provisional Application No. 62/537,596 filed on Jul. 27, 2017, all of which are incorporated herein by reference in their entirety.

BACKGROUND OF THE INVENTION

There are advantages to delivering therapeutic agents in local regions instead of systemic therapy applications, which deliver agents globally and in a dilutive fashion to an entire system. These advantages might include higher, local doses than those that could be achieved safely by systemic delivery, minimized side effects in non-target tissues, use of less agent over the life of delivery that may reduce cost and/or morbidity and targeted delivery to a site of interest. Several therapies of local delivery that might benefit from this strategy include antimicrobial, analgesic, antiseptic, chemotherapeutic, anti-inflammatory, and/or anesthetic management.

As a specific example: patients who suffer from open fractures of the extremities are susceptible to high levels of bacterial contamination, specifically those that reside in biofilms. It has been estimated that greater than 99% of bacteria in natural ecosystems (e.g., soil, dirt, human skin, GI tract, etc.) preferentially dwell in the biofilm phenotype. Mud, dirty water, debris or other exogenous vectors that harbor biofilms, or high numbers of planktonic bacteria, have potential to contaminate open fracture wounds at the time of trauma and result in biofilm-related infection. However, current antibiotic therapies, which often consist of short-term prophylactic administration, have not been optimized against biofilms. Indeed, every antibiotic on the market has been optimized against planktonic bacteria. As such, current dosing therapies may not reach sufficient blood levels to effectively eradicate biofilms. Notably, the situation is not unique to open fractures alone. Patients who receive implantable devices including total joint prosthetics, vascular devices, pacemakers, fracture fixation devices, or who undergo surgery in general are at risk of being contaminated with bacteria, including those in the biofilm phenotype.

Antimicrobial therapies that are currently in clinical use remain limited in their ability to effectively treat and prevent biofilm-related infections, in particular those that accompany the use of implanted devices. Current antibiotic therapies, including prophylactic antibiotic dosing administered systemically, may not reach sufficient levels to effectively eradicate biofilm bacteria, or, additionally, high inocula of planktonic bacteria. It is now well-known that bacteria in biofilms are resilient and can be up to 1,000 times more tolerant to antibiotics compared to their planktonic counterparts. As such, despite antibiotic intervention, biofilms may remain in a contaminated wound site and serve as a reservoir of infection.

There are many instances, including open fracture wounds, in which devices such as fracture fixation plates are implanted (either temporarily or permanently) into a patient. These implantable devices are susceptible to infection. Device-related infections are difficult to treat with clinically available antimicrobial therapies. The characteristic microbiology at the implant surface underlies the unique pathology of device-related infections. Bacteria colonize the foreign surface and evade the host immune system using several advantageous factors including the secretion of a protective extracellular polymeric (EP) matrix that envelopes the bacteria. Because of changes in the bacterial phenotype, the surface-attached biofilm community may be tolerant of antibiotics up to 1,000 times the concentration required to eradicate the metabolically active free-living planktonic forms—concentrations which are toxic to susceptible tissues like the cochlea, liver, and kidneys when delivered systemically. The implant surface thus serves as a nidus for infection harboring a community of bacteria, which adapt to the low level systemic antibiotic treatments in clinical practice.

High rates of and difficult to treat infections that are seen in clinical scenarios may be exacerbated by biofilms. For example, since Gustilo et al. defined the Type IIIB open fracture in 1984 over 30 years ago, infection rates (52%) of these fracture types have remained largely unchanged. These high rates of infection have hindered surgical outcomes and healing in soldiers and civilian patients. There are at least two main reasons proposed here as to why this unacceptably high rate of infection has continued. First, current therapies have not targeted biofilms, or high inocula of planktonic bacteria. As mentioned, biofilms have significant opportunity to contaminate open fractures or other wound sites at the time of trauma and current antibiotic therapies may provide insufficient coverage. Second, and related to the first, current therapies do not maintain sufficiently high doses/concentrations of antibiotic to prevent biofilm-related infection, in particular in an area that is not highly vascularized.

These high energy traumatic wounds and infection outcomes are highlighted in military-related healthcare. In current military conflicts, lower extremity injuries are highly common. Murray has outlined that a large percentage of lower extremity combat wounds are complicated by infection. In the military theater, rates of open fracture formation are much higher compared to the civilian population. For example, 26% of all injuries in soldiers have been reported to be fractures. Of those, 82% were open with rates of infection that have reached as high as 60%. Additional data from Brook Army Medical Center (BAMC) has shown that 40% of injured soldiers (26% of which had orthopaedic trauma) from January to June of 2006 received courses of antibiotics. Furthermore, Johnson et al. have shown that in a group of 25 soldiers who suffered Type IIIB open fractures of the tibia, 77% of their wounds had bacteria present. Taken together, these data indicate that the proposed problem is common and adversely affects wounded warriors, as well as civilian patients, and limits successful surgical outcomes.

Biofilm-related infection is of ever-growing concern across a broad spectrum of healthcare-related practices. Bacteria can either contaminate a wound or surgical site, then form into a biofilm, or well-established biofilms can contaminate these sites at the time of trauma, injury or during surgery. Furthermore, antibiotic resistance is a growing threat.

SUMMARY OF THE INVENTION

To address these growing concerns, a therapeutic agent (e.g., antimicrobial) releasing pouch has been developed for use in conjunction with a variety of implantable devices, body locations, or can be used as a standalone product in wounds or surgical sites.

Preliminary in vitro tests have shown efficacy by eradicating both biofilm and planktonic bacteria in the presence of the antimicrobial releasing pouch. For example, under flow conditions (fluid exchange rate of approximately 14%/hr) in brain heart infusion broth, the pouch (filled with 15 mL of PBS that contained 70 mg/mL fosfomycin, 25 mg/mL gentamicin and 2 mg/mL rifampin) was able to fully eradicate $10^9$ colony forming units (CFU) of methicillin-resistant *Staphylococcus aureus* (MRSA) within a 24 hr period. In the presence of serum, the same antibiotic combination in the pouch was able to reduce MRSA biofilms by more than 6 $log_{10}$ units in 24 hr. In vivo testing in a sheep model of Type IIIB open fracture, wherein the pouch was placed subdermally yet directly over an implant site that contained $10^9$ CFU of MRSA in biofilms, showed the ability of the pouch to treat and prevent biofilm implant-related infection.

In one embodiment, the present invention provides a therapeutic delivery device that will provide the ability to release high doses of a therapeutic compound (e.g., an antibiotic) in a local area (important for effective biofilm eradication or eradication of high numbers of planktonic bacteria), sustain that high dose release with a percutaneous port that will allow for reloadability of the device, and be versatile for use with multiple types of antimicrobials and/or implant systems. A rate determining/controlled release membrane is used to decrease the molecular mobility of the therapeutic compounds thereby controlling the therapeutic release profile. Materials for this membrane might broadly include nano- and micro-porous size exclusion membranes (e.g., semi-permeable membranes, micromachined polymers or metals, etc.), hydrophilic polymer systems, or hydrogels.

In another embodiment, the present invention provides a therapeutic delivery device that includes a body including a rate determining membrane. The body defines an internal reservoir and is configured to be deployed subcutaneously. The device also includes a port having a cap. The port is in fluid communication with the reservoir and is configured to extend percutaneously from the body to the surrounding environment such that the cap is externally exposed thereby allowing a user to refill the reservoir via the port.

In one construction, the therapeutic delivery device may include an outer protective sleeve encasing the pouch to, for example, protect the membrane from punctures or bursting.

In another construction, the outer protective sleeve may be distinct from the membrane of the pouch or the outer protective sleeve may be combined with the membrane of the pouch (e.g., in a double-walled system or composite membrane).

In a further construction, the outer protective sleeve may be constructed from a fibrous material or fabric with a greater therapeutic permeability than, for example, a rate determining membrane. The outer sleeve may contain features to allow for attachment to tissue through clinically available fasteners (e.g., sutures, staples, pins, unidirectional barbed sutures, etc.). The outer sleeve may include radiopaque markers for positioning, locating, or adjusting with fluoroscopy or X-ray collection.

In yet another embodiment, the present invention provides a method for deploying a therapeutic delivery device within a patient including inserting the pouch into the patient such that a body of the pouch that includes a rate determining membrane at least partially defining the bounds of a reservoir is disposed subcutaneously within the patient. In addition, a port of the pouch that is fluidly coupled to the reservoir extends from the body percutaneously to the surrounding environment. The method also includes delivering a therapeutic agent contained with the reservoir to tissue and fluids of the patient surrounding the body via the rate determining membrane. The method also includes refilling the reservoir with the therapeutic agent via the port in order to continue delivering therapeutic agent. The method also includes removing the pouch from the patient after the reservoir has been substantially emptied.

In a further embodiment, the invention provides a therapeutic delivery device comprising a body defining an internal reservoir for a therapeutic agent and configured to be deployed subcutaneously near a surgical site, the body including a first membrane for controlled release of the therapeutic agent to the surgical site, a port including a cap and a stem, the port in fluid communication with the reservoir and being configured such that the cap allows a user to refill the reservoir via the port, and a sleeve configured to encapsulate the body, the sleeve including a tab region configured to receive a fastener to anchor the body in position relative to the surgical site, the sleeve including a second membrane to deliver the therapeutic agent from the body to the surgical site.

In another embodiment, the invention provides a therapeutic delivery device comprising a body defining an internal reservoir for receiving a therapeutic agent and configured to be deployed subcutaneously near a surgical site, the body including a first membrane for providing a controlled release of the therapeutic agent to the surgical site, a port in fluid communication with the reservoir, a sleeve configured to encapsulate the body, the sleeve including a tab region configured to receive a fastener, the sleeve including a second membrane to deliver the therapeutic agent from the body to the surgical site, and a rigid housing configured to support the body and a portion of the sleeve, the tab region extending from a gap in the rigid housing, the rigid housing configured to release the body and the sleeve after the fastener to anchor the body and the sleeve in position relative to the surgical site.

In another embodiment, the invention provides a method for deploying a therapeutic delivery device within a patient, the therapeutic delivery device including a body, a port, and a sleeve. The method comprises applying a rigid housing over the therapeutic delivery device, inserting the rigid housing into the patient through an incision and positioning the body adjacent to a treatment site, anchoring the therapeutic delivery device, releasing the rigid housing from the therapeutic delivery device, removing the rigid housing through the incision, positioning the port for external access, filling the therapeutic delivery device with a therapeutic agent via the port, delivering the therapeutic agent in a controlled manner to the treatment site, and removing the therapeutic delivery device from the patient.

Other features and aspects of the invention will become apparent by consideration of the following detailed description and accompanying drawings.

BRIEF DESCRIPTION OF THE DRAWINGS

FIGS. 14A-B are graphs illustrating release profiles of an exemplary embodiment of the therapeutic delivery device.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting.

DETAILED DESCRIPTION

The terms rate determining membrane and control release membrane broadly describe membranes which can be used with embodiments of the invention, rather than a more narrow term "semi-permeable membrane". Nearly all membranes fit broadly into one of two classes: Size exclusion membranes and affinity membranes. Size exclusion membranes are semi-permeable membranes which use physical pores to selectively pass solutes. These include: ultrafiltration membranes, microfiltration membranes, nanofiltration membranes, and dialysis membranes. Affinity membranes, on the other hand, use molecular affinity interactions between the solute and the membrane components or functional groups to slow down the solute diffusion rate within the membrane. Affinity membranes are much less common but include hydrogels, polymer systems, and functionalized polymer systems. If selected carefully any number of these membranes or membrane types might be used in the pouch to achieve the target therapeutic delivery profile.

FIGS. 1-4 illustrate a therapeutic delivery device (e.g., pouch) 10 configured to provide a therapeutic agents (e.g., antibiotics, antimicrobials, anti-tumor agents, steroids, analgesics, anti-inflammatories, etc.) to a wound site, surgical site or body cavity. In one embodiment, the therapeutic delivery device 10 is configured as an antimicrobial pouch that is placed within a wound/surgical site to deliver an antimicrobial agent within the wound/surgical site to prevent infections. Examples of such wounds/surgical sites include implants/implant sites, abscesses, chronically infected wounds, and other localized infections. In one example, the therapeutic delivery device 10 may be placed within a wound/surgical site after an open fracture of a bone within one of a patient's extremities (e.g., reduced with a fixation plate) to provide high doses of antimicrobial agents over an extended period of time to prevent and treat biofilm infection.

Figure 1:
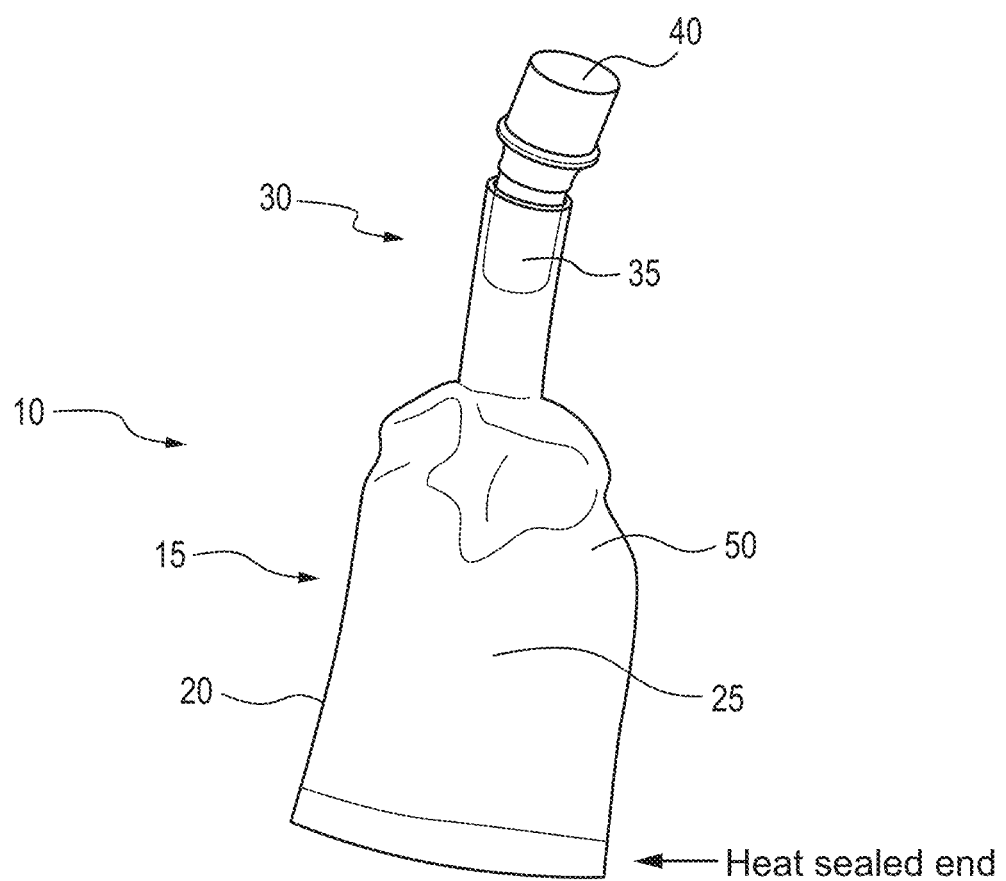
FIG. 1 illustrates a therapeutic delivery device according to an embodiment of the present invention.
Figure 2:
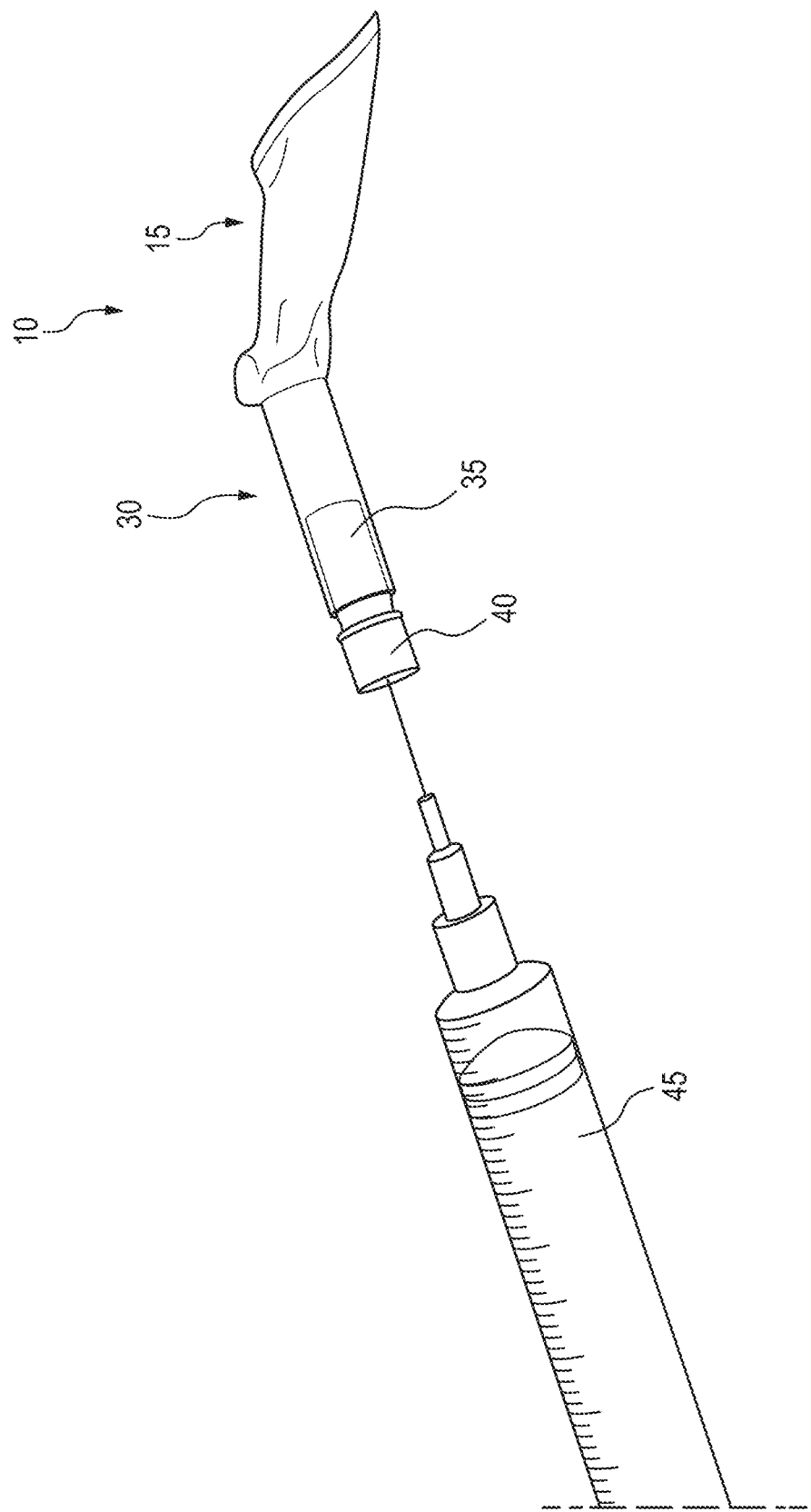
FIG. 2 illustrates the therapeutic delivery device of FIG. 1 being filled with a solution.

With reference to FIG. 1, the therapeutic delivery device 10 includes a body 15 having an outer wall 20 that defines a reservoir 25 within the body 15. The device 10 includes a port 30 coupled to the body 15. The port 30 includes a stem 35 and an injection cap 40. The stem 35 extends between the body 15 and the injection cap 40. The port 30 is in fluid communication with the reservoir 25 such that a liquid antimicrobial agent may be introduced into the reservoir 25 via the injection cap 40. In the illustrated embodiment, the injection cap 40 is configured to seal the reservoir 25 from outside contaminants, but receive the needle of a syringe 45 such that the reservoir 25 may be refilled or replenished (FIG. 2). The injection cap 40 is constructed of a self-sealing material such that any aperture created by inserting the syringe is automatically sealed when the syringe is withdrawn. However, in other embodiments, the injection cap 40 may be a needleless injection cap 40 such that materials may be introduced using a needleless injection method without exposing the reservoir 25 to contaminants.

With continued reference to FIG. 1, the outer wall 20 of the body 15 is constructed from at least one membrane 50 (such as, a rate determining or control release membrane, for example, a nano and micro porous size exclusion membranes such as semi-permeable membranes or micromachined polymers or metals, affinity membranes such as hydrogels, polymer systems, and functionalized polymer systems, etc.) such that the reservoir 25 selectively communicates antimicrobial agents with the surrounding environment. That is, the membrane 50 facilitates a controlled release of the antimicrobial agents. In one construction, the membrane can comprise ethylene vinyl acetate or a polyurethane film such as Medifilm® from Mylan.

In the illustrated embodiment, the body 15 has an end of the outer wall 20 that is opposite the port 30 heat sealed to at least partially enclose the reservoir 25. However, other methods of sealing the body 15 in order to form an internal reservoir 25 may be utilized. In an exemplary embodiment, the membrane 50 is a semi-permeable size exclusion membrane with a molecular cut off of approximately 0.1-0.5 kDaltons (e.g., based on the molecular weights of cefepime, levofloxacin, fosfomycin, gentamicin, or rifampin). However, this embodiment is merely exemplary and the molecular weight cut off of the semi-permeable membrane 50 may be selected/customized in order to function with other therapeutic agents. For example, membranes in the nanoand ultra-filtration ranges with pore sizes from approximately 1-100 nm and molecular cutoffs from 1-14 kDa may be used. The semi-permeable membrane 50, in this example, is configured to enable delivery of the antimicrobial/therapeutic agent to the surrounding tissue according to an elution profile as defined by characteristics of the semi-permeable membrane 50. For example, the semi-permeable membrane 50 may be configured to regulate molecular mobility and slow down the diffusion of the liquid antimicrobial agent through the semi-permeable membrane 50. In other examples, the membrane 50 may create a steady-state elution profile or a variable rate elution profile, among others. In any case, the elution profile is set such that a high concentration of the antimicrobial agent is maintained within the surgical site for a predetermined amount of time to prevent local infection. In addition, the device 10 can be modular such that rate of release (based on membrane or other material selection) can be rapid, given as a bolus dose, which may be beneficial to eradicate biofilms quickly, or throttled to deliver lower doses over a longer period of time, which may be of interest for an alternate indication such as pain management. Other factors that may be utilized to control elution profiles include the density of pores on the semi-permeable membrane 50 and the thickness of the semi-permeable membrane 50.

In the illustrated embodiment, the stem 35 is a non-permeable tube interconnecting the injection cap 40 and the body 15. As such, the therapeutic agent is delivered from the injection cap 40 to the body 15 through the tube. In other embodiments, however, the stem 35 may be at least partially constructed from a membrane (e.g., a similar membrane as described above) such that the therapeutic agent is delivered to a greater volume within the wound site. For example, in this configuration, the therapeutic agent would further be delivered directly to the areas surrounding the percutaneous incision to prevent surgical site infection.

In other constructions, the stem 35 may be variable based on the application. For example, the length of the stem may be varied, the type of connection may be varied (e.g., needled or needleless connection), and/or can be made of various materials (e.g., permeable or non-permeable materials). In addition, the device 10 may include multiple stems 35 to, for example, facilitate the introduction of different therapeutic agents or to form an inlet to fill the reservoir and a separate outlet to empty the reservoir.

In another construction, the port 30 and, more specifically, the stem 35, may extend through the reservoir 25 of the body 15 to provide structural support to the body 15, aid in maintaining a more uniform body profile (e.g., when the reservoir is empty), and to facilitate more even filling of the reservoir 25. In this embodiment, at least a portion of the stem 35 (e.g., the portion lying within the reservoir 25) includes apertures, perforations, permeable membrane portions, or other means for fluid communication between the stem 35 and the reservoir 25.

The therapeutic delivery device 10 may vary in size. In one example, the body 15 is approximately 10 cm long. However, all aspects of the device 10 may be tailored for specific uses and specific placements within the anatomy. For example, the size of the body 15 or the length of the stem 35 may be varied (e.g., made longer so the device 10 may be placed deeper into tissue). In addition, an introducer device may be used to aid in deployment of the device 10 in applications when a separate surgery is not being performed (e.g., in the case of treatment as opposed to prophylaxis) such as treatment of osteomyelitis or infections associated with previously implanted devices.

The therapeutic delivery device 10 has been tested for efficacy in treating biofilms. In one test, the device 10 was filled with an antibiotic solution and placed in test tubes that contained either $10^8$ colony forming units (CFU)/mL or well-established biofilms of methicillin-resistant *Staphylococcus aureus* (MRSA). Fresh bacteria and solution were added to the test tubes daily for 10 days and quantified each day. With n=6 repeats, it was shown that planktonic and biofilm bacteria were eradicated completely.

With reference to FIGS. 14A-B, the elution profile of an exemplary 12-14 kDa molecular weight cutoff semi-permeable membrane 50 was also tested and determined using an established flow cell system. The therapeutic delivery device 10 was filled with 15 mL of antibiotic solution (a combination of fosfomycin, gentamicin and rifampin) with varying concentrations, and placed into a chamber of a flow cell unit that contained 50 mL of phosphate-buffered saline (PBS). PBS was flowed through the flow cell unit (turnover rate of approximately 14%/hr) to create a dynamic environment. Samples of eluate were collected every 2 hrs for 24 hrs and it was shown that concentrations of rifampin increased and decreased over the 24 hr period as hypothesized.

Figure 15:
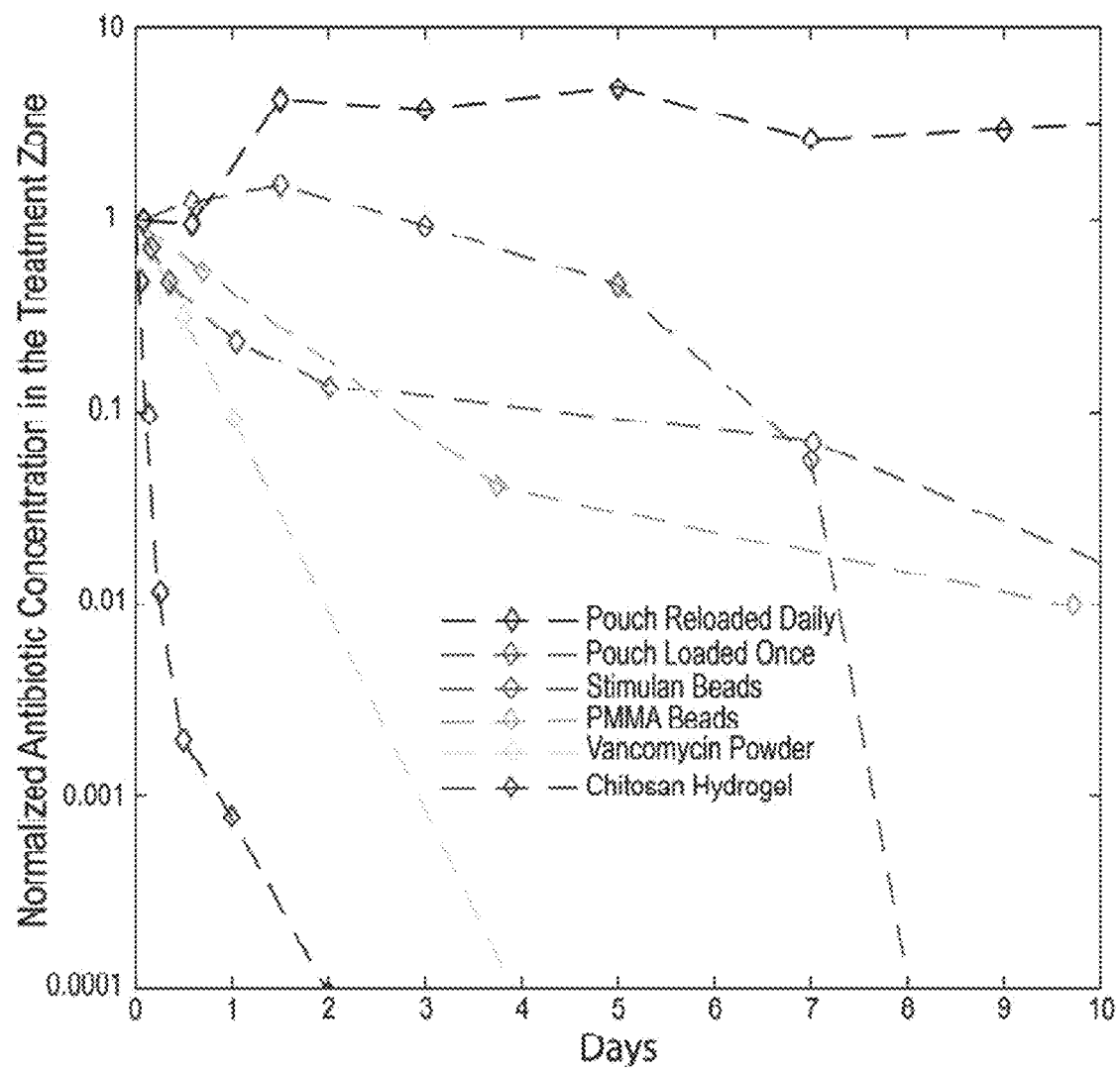
FIG. 15 graphically illustrates improved release profiles of an exemplary embodiment of the therapeutic delivery device compared to clinical standards.

With reference to FIG. 15, additional release profiles were determined with gentamicin over a period of 10 days. Samples of eluate were collected every 24 hrs. In one instance, the device was reloaded with fresh antibiotic every 24 hrs (black line). In another instance, the device was loaded a single time (green line). Release profiles were compared to clinical standards of care that offer local, high dose release, but cannot be reloaded (red, orange, turquoise and purple lines).

Figure 3:
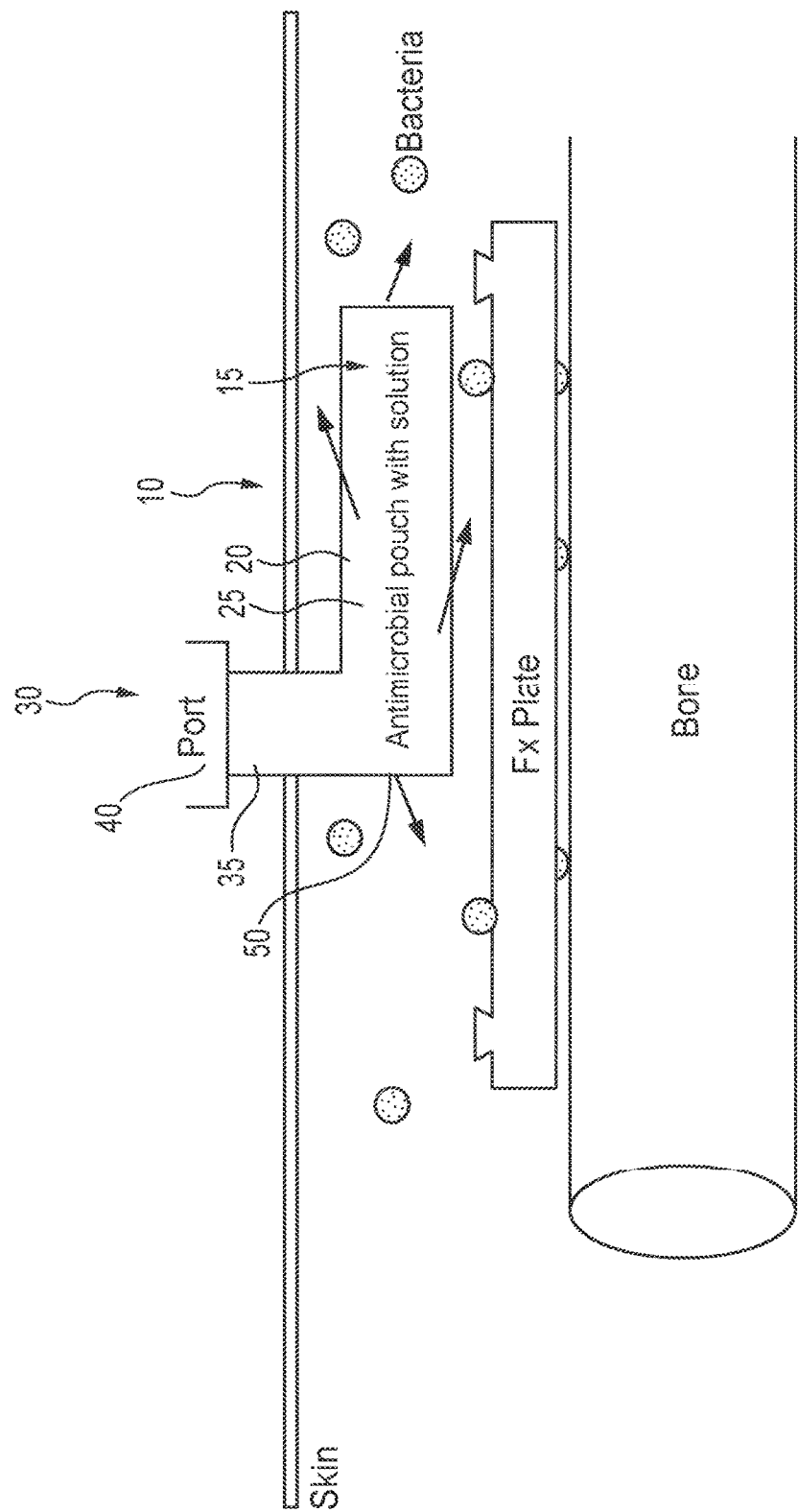
FIG. 3 is a schematic representation of the therapeutic delivery device of FIG. 1 disposed within a patient.

FIG. 3 illustrates a schematic representation of the therapeutic delivery device 10 deployed within a fracture site in which the patient's fracture has been reduced and fixated using a fixation plate. This type of wound site and the fracture plates are susceptible to infection, particularly from infectious biofilms (e.g., non-planktonic bacteria such as MRSA). In order to provide a strong therapeutic effect, the body 15 of the device 10 is positioned entirely within the patient (i.e., beneath the skin) to deliver the therapeutic agent contained within the reservoir 25 to the wound site. Such a configuration enables a high concentration of therapeutic agents to be delivered and maintained locally in order to treat or prevent infection. In this configuration, the stem 35 of the port 30 extends through an incision (i.e., extends percutaneously) to expose the injection cap 40 to the surrounding environment, thereby granting a user (e.g., the patient, an aide, a medical practitioner, etc.) access to the injection cap 40. This allows the user to refill the reservoir 25 as desired or instructed to enable long-term therapeutic agent delivery (e.g., hours, days, weeks, etc.) to continue to treat and prevent infection.

Figure 4:
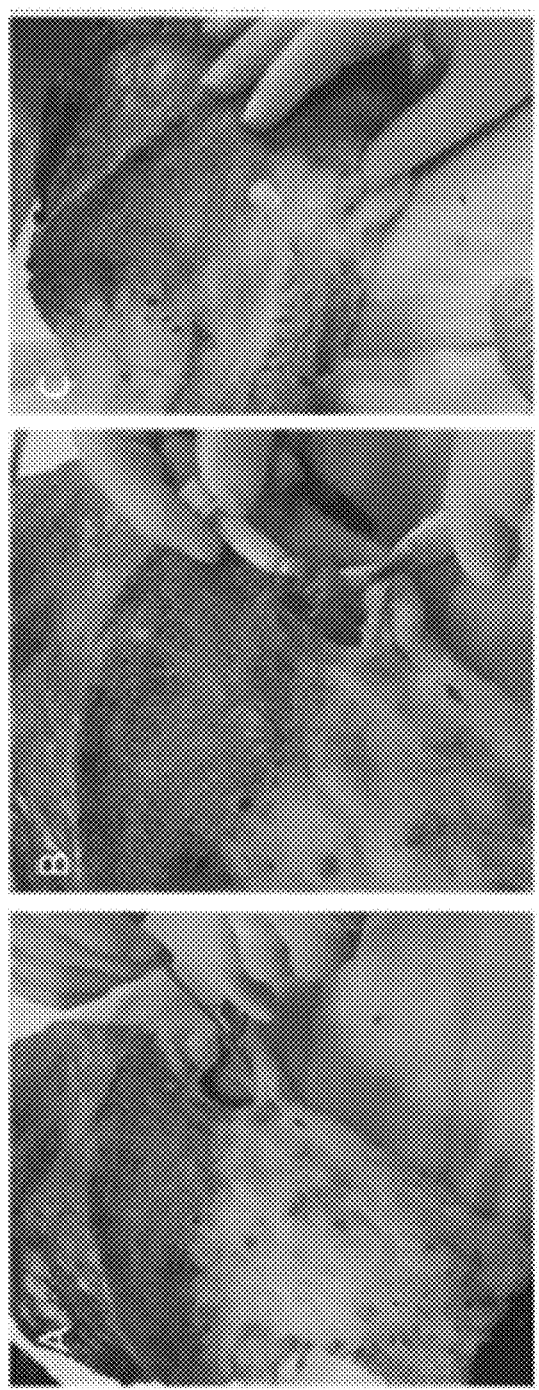
FIG. 4 is a set of images illustrating exemplary use of the therapeutic delivery device.
Figure 4:
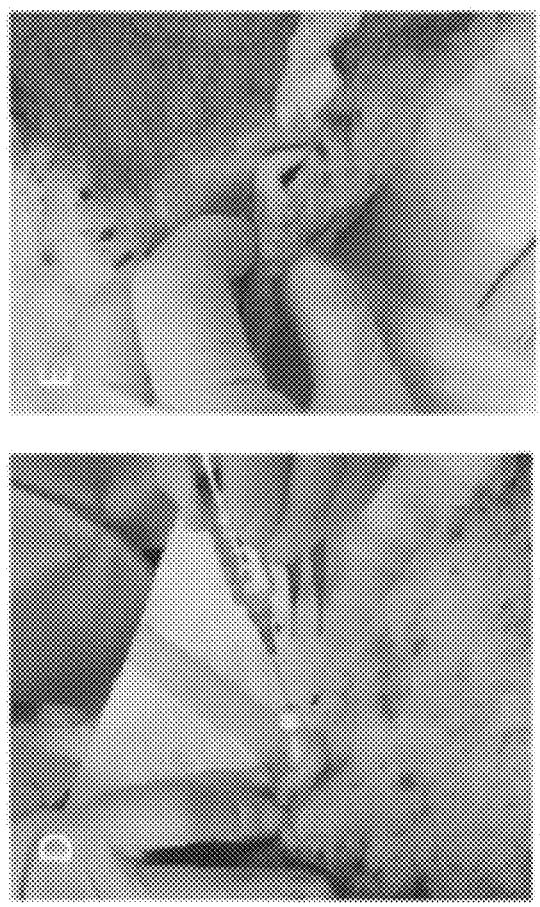

FIG. 4 illustrates deployment and use of the exemplary therapeutic delivery device 10 within a test subject. As seen in image A of FIG. 4, the first step includes creating an incision to deploy the therapeutic delivery device 10 within the subject. In other embodiments, however, a previously made incision (e.g., a surgical incision or would site) may be utilized. In a subsequent step, image B, the body 15 of the device 10 is inserted subcutaneously within the subject, with the stem 35 of the port 30 extending percutaneously to expose the injection cap 40 to the environment. In this image, the reservoir 25 of the device 10 may be empty in order to reduce the size of the incision necessary to deploy the device 10, or the reservoir 25 may be at least partially filled when the device 10 is deployed. In the next image C, a suture line is used to close the tissue surrounding the body 15 and the stem 35 of the port 30. In a subsequent step (image D), the reservoir 25 is filled using a syringe to deliver therapeutic agent to the reservoir 25 via the self-sealing injection cap 40 after at least a portion of the therapeutic agent has been delivered to the wound site. It should be noted that this step may be repeated as necessary during the duration of deployment of the device 10. In a final step, illustrated in image E, the device 10 is removed from the patient. In this step, the device 10 may be emptied (e.g., via full depletion of the reservoir 25 during deployment or by withdrawing remaining therapeutic agent via the injection cap 40 with a syringe) to reduce the volume/cross-sectional area of the body 15. This enables removal via the incision, which may be substantially smaller due to healing, with limited difficulty. In some cases, it may be necessary to remove one or more sutures in order to remove the device 10, but the size of the incision necessary for removal remains relatively small.

Figure 5C:
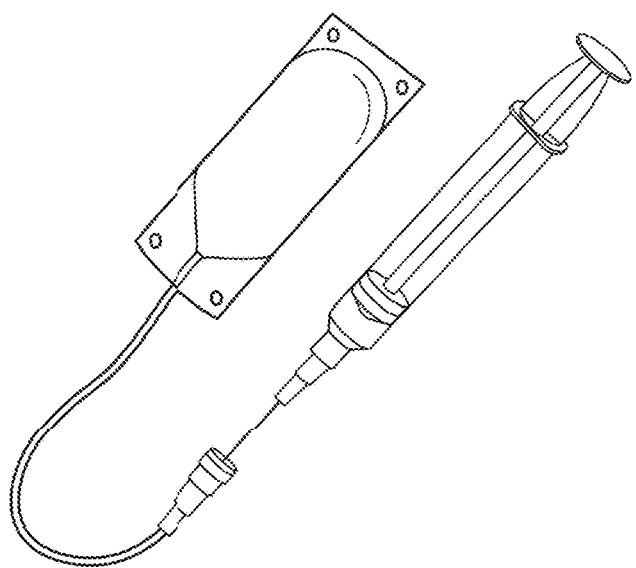
FIG. 5C illustrates the therapeutic delivery device of FIG. 5A that is filled and coupled to a fluid source.
Figure 5B:
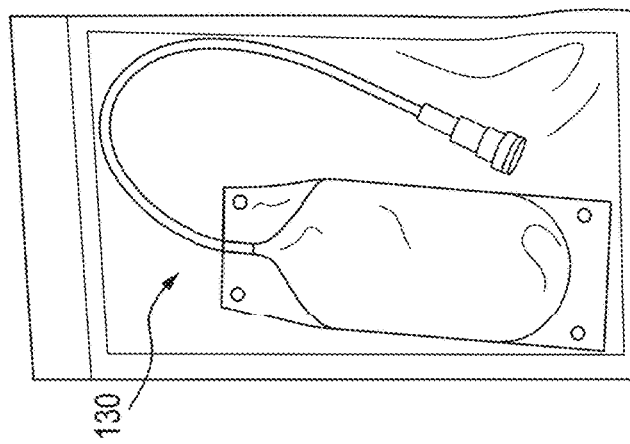
FIG. 5B illustrates the therapeutic delivery device of FIG. 5A disposed within sterilized packaging.
Figure 5A:
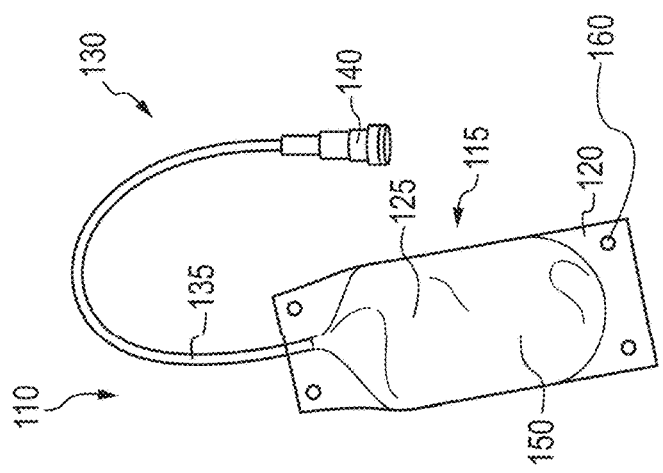
FIG. 5A illustrates a therapeutic delivery device according to an embodiment of the present invention.

FIGS. 5A-C illustrates a therapeutic delivery device 110 according to another embodiment of the present invention. The device 110 is substantially similar to the device 10 described above. The features of the device 110 that are substantially the same as the features of the device 10 are indicated by the same reference numerals plus "100." The following description focuses primarily on the differences between the device 110 and the device 10. However, it should be noted that features from the device 110 may be used on the device 10 and vice versa.

The therapeutic delivery device 110 includes a body 115 having an outer wall 120 that defines a reservoir 125 within the body 115. A port 130 is coupled to the body 115 and includes a stem 135 extending between the body 115 and an injection cap 140. The body 115 includes a rate determining membrane 150 having a molecular weight cut off of 12-14 kDa (e.g., a cellulose membrane). In this embodiment, the outer wall 120 is sealed using a flexible medical grade adhesive (e.g., flexible medical grade cyanoacrylate Loctite® 4902). The device 110 further includes holes 160 disposed in corners of the body 115 (e.g., on seams of the body 115) for receiving sutures to anchor the device 10 in position. FIG. 5B illustrates placement of the antimicrobial pouch 110 within a Tyvek® peel-pouch 180 to demonstrate sterilization feasibility via ethylene oxide. FIG. 5C illustrates a syringe coupled to the injection cap 140 and filling the body 115 with a therapeutic agent as the body 115 is shown in an expanded or filled state.

Figure 6B:
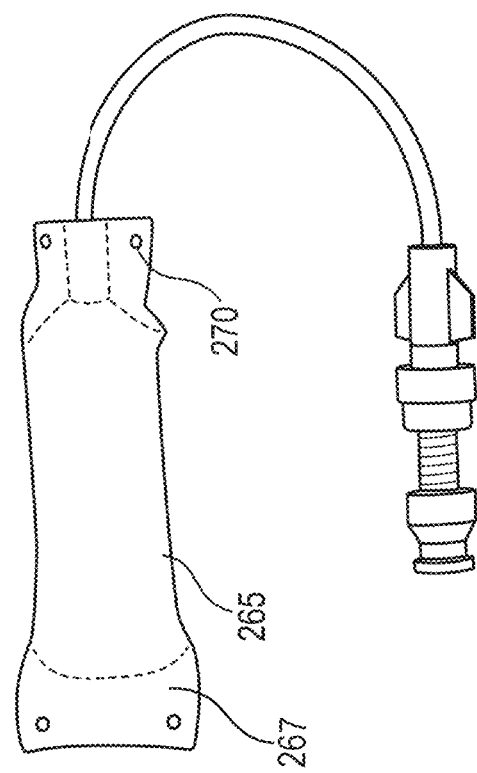
FIG. 6B illustrates the therapeutic delivery device of FIG. 6A further including a protective sleeve.
Figure 6A:
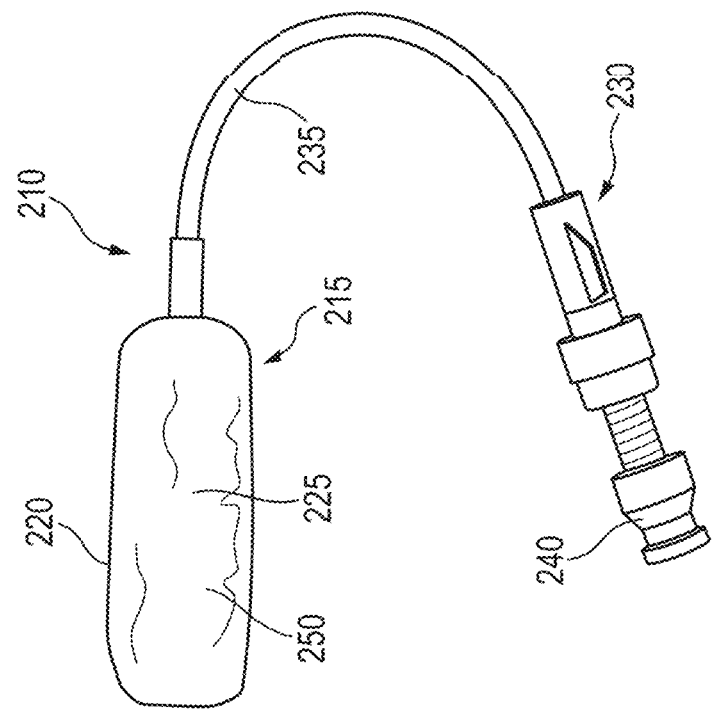
FIG. 6A illustrates a therapeutic delivery device according to an embodiment of the present invention.
Figure 7:
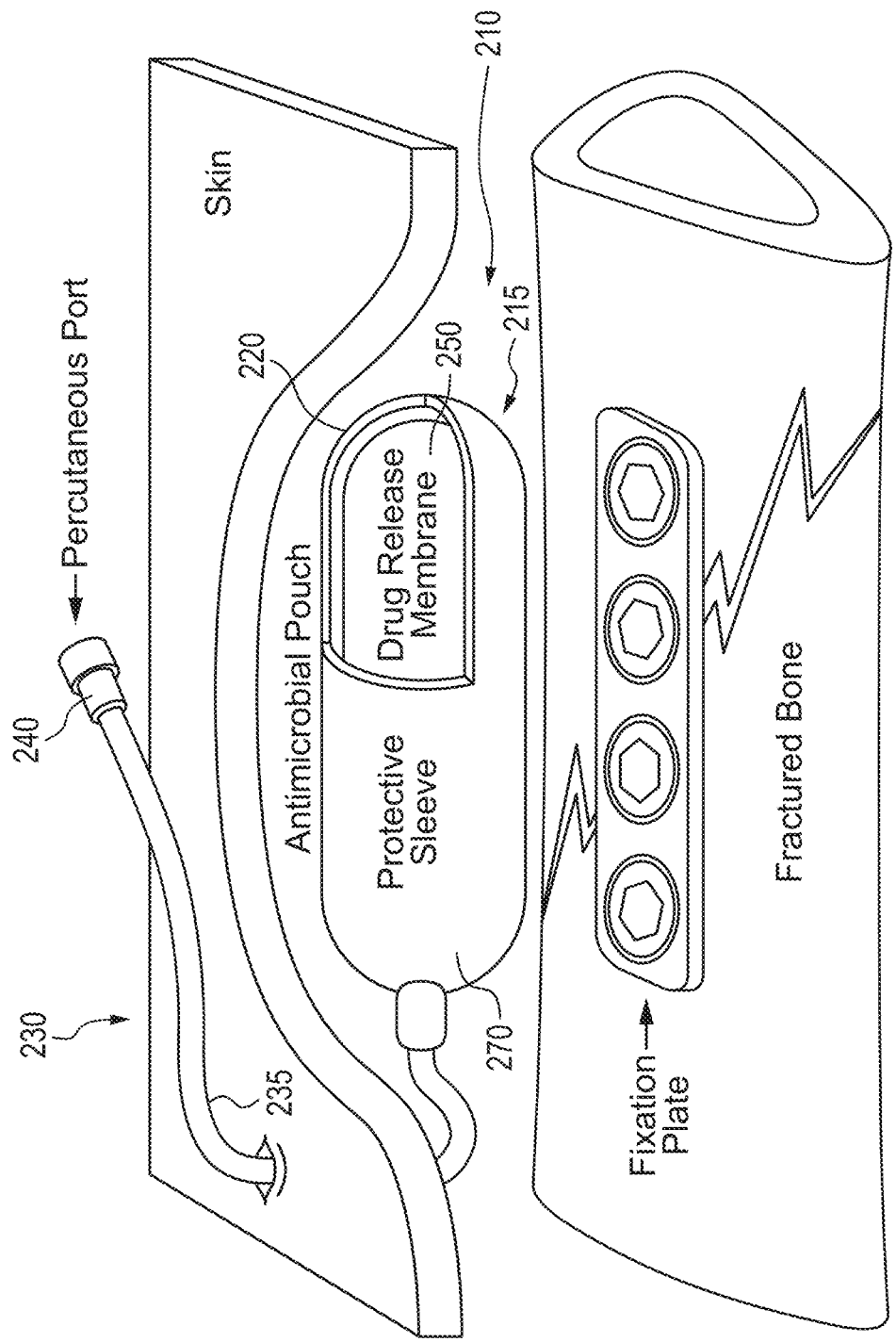
FIG. 7 is a schematic representation of the therapeutic delivery device of FIGS. 6A and 6B disposed within a patient.

FIGS. 6A-B and 7 illustrate a therapeutic delivery device 210 according to another embodiment of the present invention. The device 210 is substantially similar to the devices 10, 110 described above. The features of the device 210 that are substantially the same as the features of the devices 10, 110 are indicated by the same reference numerals as device 10 plus "200." The follow description focuses primarily on the differences between the device 210 and the devices 10, 110. However, it should be noted that features from the device 210 may be used on the devices 10, 110 and vice versa.

The device 210 includes a body 215 having an outer wall 220 that defines a reservoir 225 within the body 215. A port 230 is coupled to the body 215 and includes a stem 235 extending between the body 215 and an injection cap 240. In one construction, the injection cap 240 is a needle-free injection valve (e.g., a SmartSite™ needle-free injection valve). The body 215 is closed using nylon material, and the stem 235 is secured to the body 215 using the same nylon material.

The device 210 also includes a sleeve 265 encapsulating the body 215 and at least a portion of the port 230 (e.g., a portion of the stem 235). In one construction, the sleeve 265 is constructed from a highly porous polymer material or a fibrous material like a fabric weave, braid, kit, or felt (e.g., such that the release rate of the sleeve is greater than the release rate of the membrane 250) and may include holes 270 (e.g., as a site for attaching mechanical anchors such as sutures, unidirectional barbed sutures, staples, pins, etc. that mechanically couple the device 210 to a particular location in the patient) disposed on, for example, tabs 267 of the sleeve 265. The tabs 267 provide a boundary or extension in certain areas of the sleeve 265. In the illustrated embodiment, the tabs 267 are positioned at opposite ends of the sleeve 265, however it is noted that the tabs 267 may be positioned as needed depending on application and implantation techniques used. In alternate embodiments, the sleeve 265 may include other permeable or semi-permeable materials, such as a porous material that prevents/discourages tissue ingrowth (e.g., ADAPTIC TOUCH™), may be used in place of or in addition to the nylon plain weave fabric such that the rate of release or elution profile of the therapeutic agent is further effected by the sleeve 265. In another alternate embodiment, the sleeve 265 and the membrane 250 may be fused together (i.e., the sleeve 265 and the membrane 250 form a composite membrane such as a thin film composite membrane). Such an embodiment may also include additional sleeves 265 and/or membranes forming additional layers in the composite membrane.

The sleeve 265 can be configured in the same way as the membrane 50 described above to effect or control the release of the therapeutic agent. Furthermore, the sleeve 265 protects the membrane 250 from contact with abrasive objects that might cause a puncture such as jagged bone, surgical instruments, fixation hardware, or bone cement, among others. In addition, the sleeve 265 protects the body 215 from bursting under loads (e.g., overfilling, application of pressure to body 215, etc.). In some embodiments, the sleeve 265 includes radiopaque markers for positioning, locating, or adjusting the device 210 within the patient via fluoroscopy (e.g., C-arm imaging) or X-ray collection.

Figure 8A:
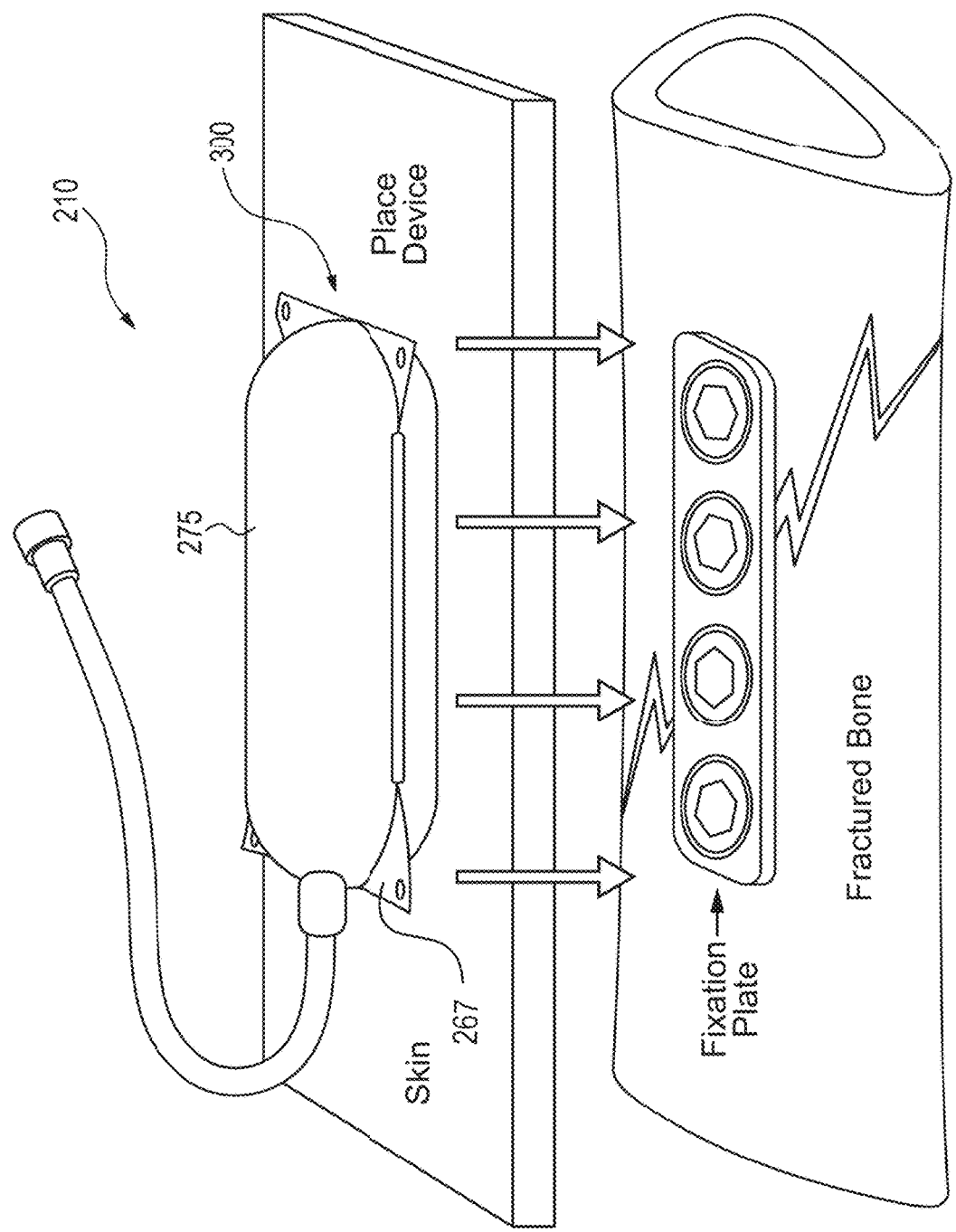
FIGS. 8A-C schematically illustrate a rigid housing for use with the therapeutic delivery device illustrated in FIGS. 6A-B.
Figure 8B:
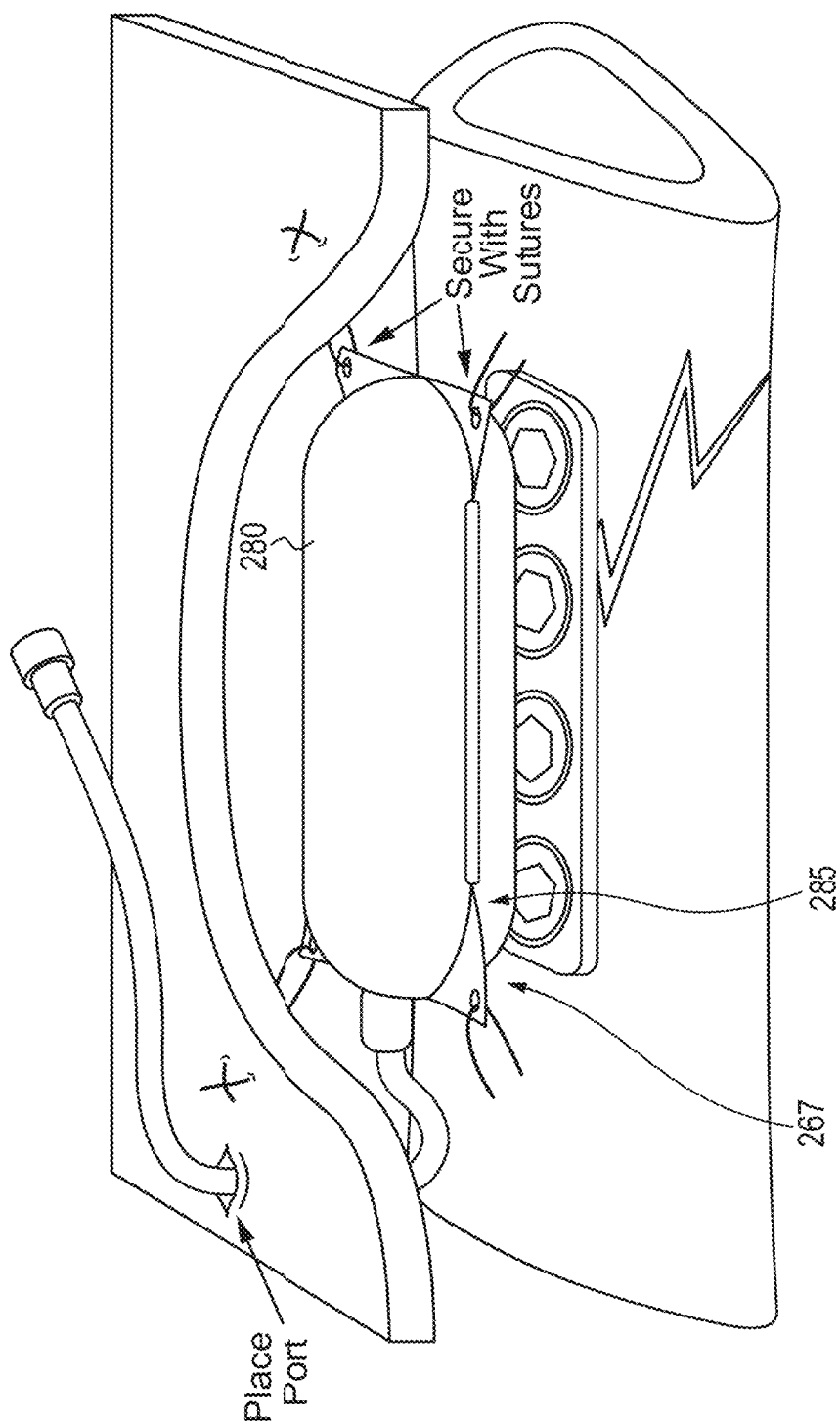
Figure 8C:
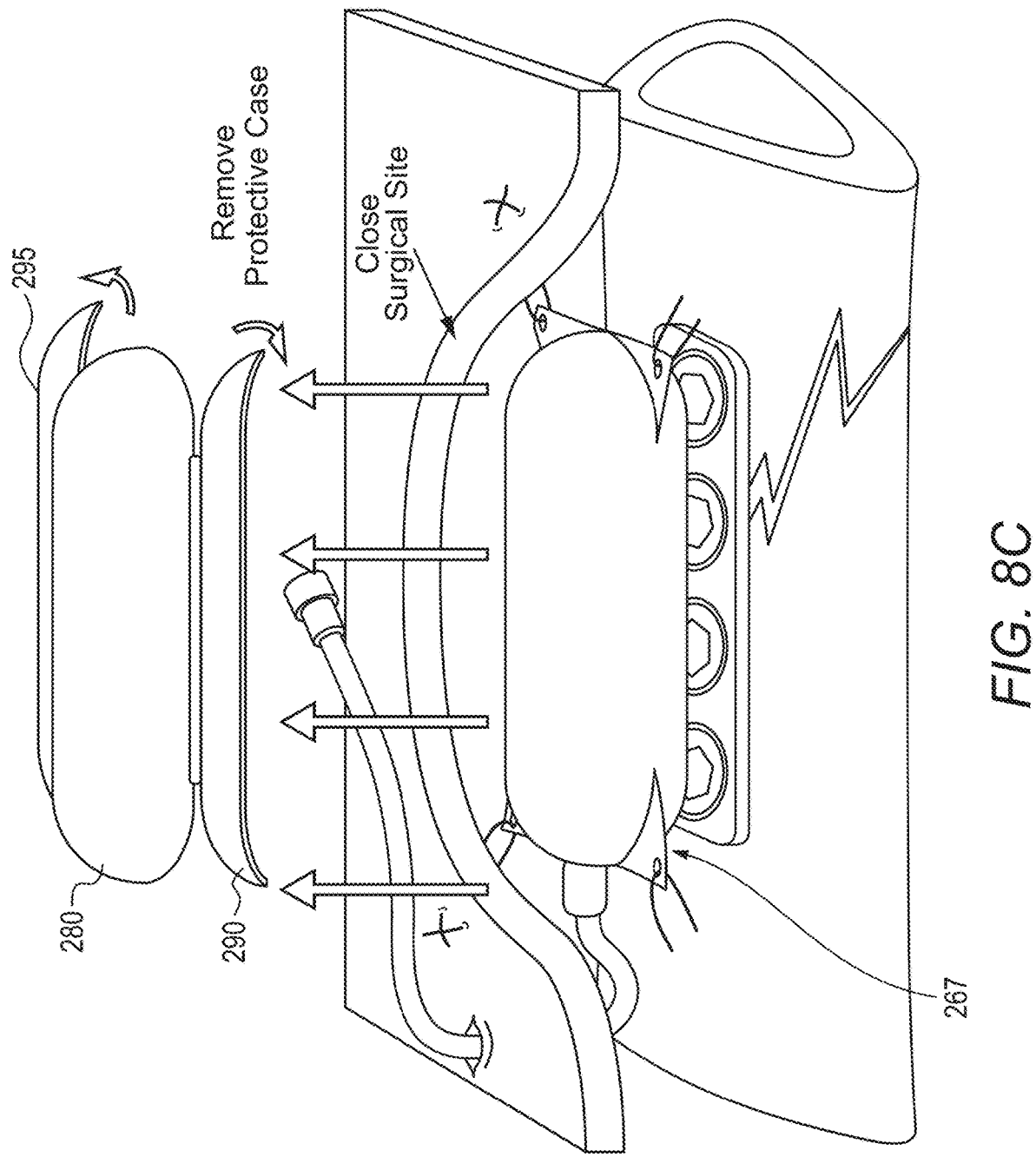

In this embodiment, the device 210 includes a removable rigid housing 275 as illustrated in FIGS. 8A-C. The rigid housing 275 is configured to receive the body 215 and provides protection to the body 215 and sleeve 265 from puncture or damage during implantation. The housing 275 includes an upper portion 280 and a lower portion 285 coupled to the upper portion 280. The lower portion 285 is divided into a first portion 290 and a second portion 295. As illustrated, the upper portion 280 and the lower portion 285 are hingedly coupled, and more particularly, the first portion 290 is hingedly coupled to the upper portion 280 at a first side of the housing 275, and the second portion 295 is hingedly coupled to the upper portion 280 at a second side of the housing 275 opposite the first side. This configuration allows the first portion 290 and the second portion 295 to separate (i.e., open) upon removal of the housing 275.

With reference to FIGS. 8A-B, the rigid housing 275 provides a slight gap 300 between the upper portion 280 and the lower portion 285. The gap 300 allows the tabs 267 on the sleeve 265 to extend from the housing 275. As noted above, the tabs 267 include holes 270 which are used to anchor the sleeve 265 in position by suturing or other mechanical fasteners without risk of needle damage to the device 210. Once the surgical site is ready for closure, the housing 275 can be removed and discarded (FIG. 8C). In other constructions, the rigid housing 275 may be configured as a single piece or multi-part with alternative coupling mechanisms. The housing 275 may include lettering directing clinicians for its removal before surgical site closure.

Figure 9A:
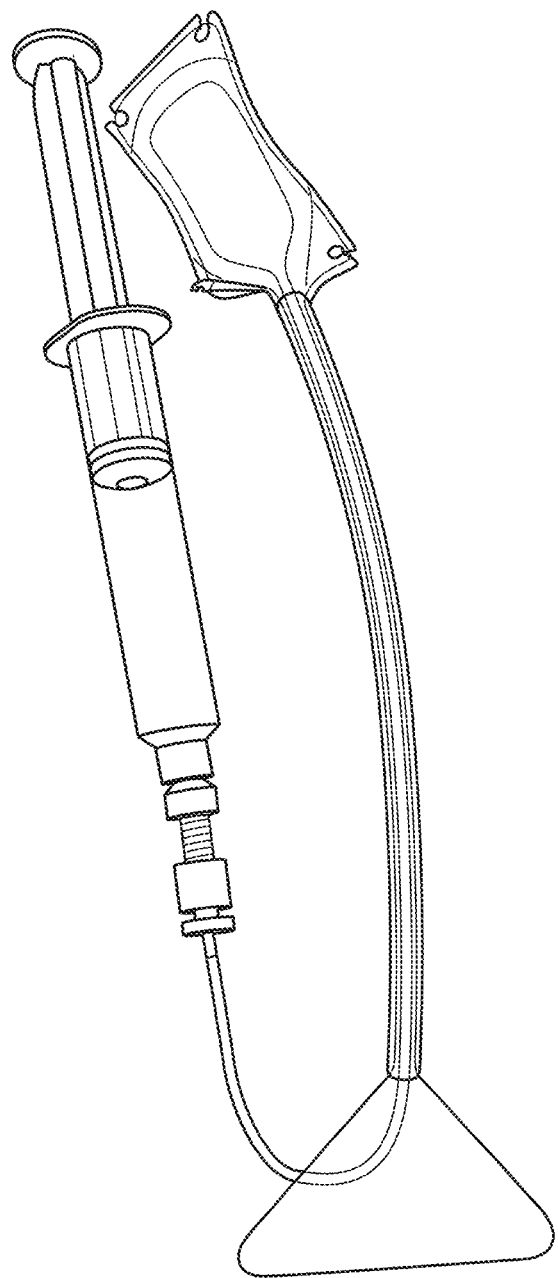
FIG. 9A illustrates the therapeutic delivery device of FIGS. 6A-B including a drawstring and dual lumen port.
Figure 9C:
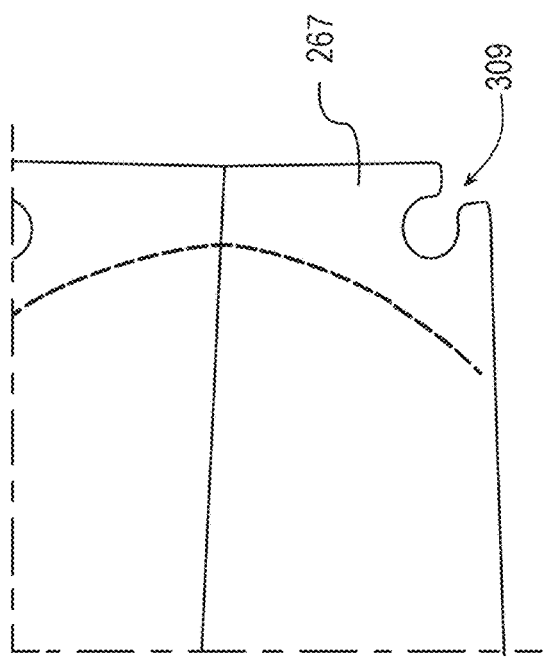
FIGS. 9B-C illustrate enlarged portions of a tab region of the sleeve of FIG. 6B.
Figure 9B:
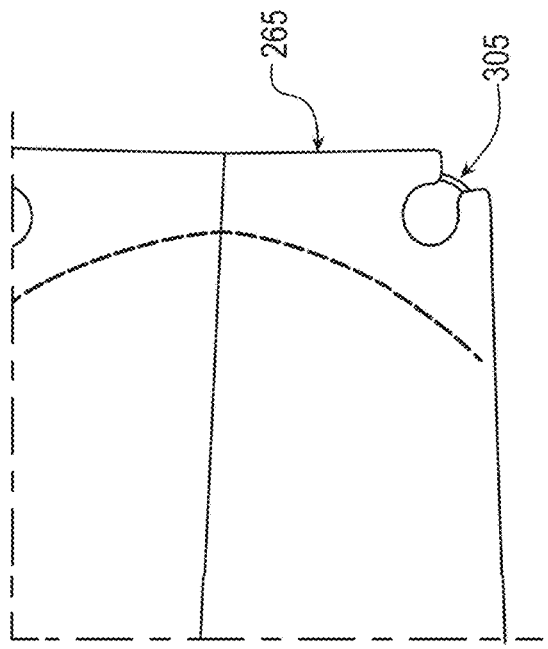
Figure 9D:
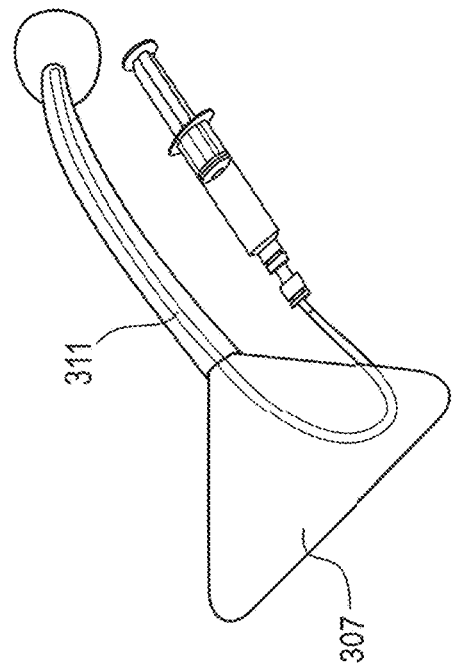
FIG. 9D illustrates an enlarged view of a pull tab and dual lumen port.
Figure 9F:
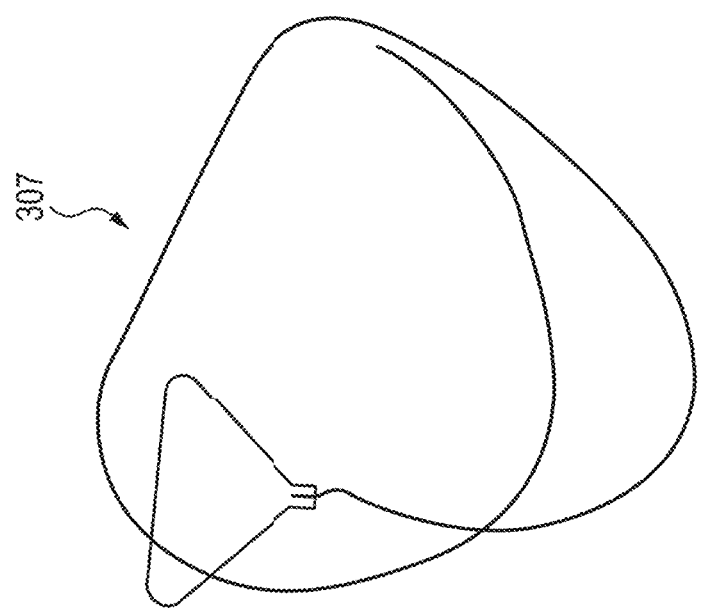
FIG. 9F illustrates the drawstring and pull tab.
Figure 9E:
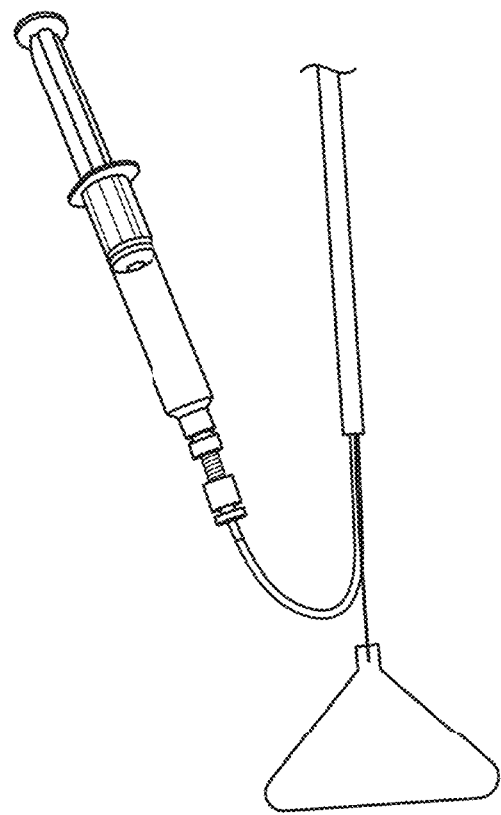
FIG. 9E illustrates the therapeutic delivery device of FIGS. 6A-B including a drawstring and dual lumen port.

With reference to FIGS. 9A-F, the sleeve 265 may be modified to include slits or openings in the tabs 267 at each of the holes 270 (FIGS. 9B-C). In this configuration, a drawstring 305 (FIG. 9F) encircles the sleeve 265 to facilitate removal of the device 210. To accommodate this construction, the stem 235 has a double lumen where one lumen is used for filling, refilling, and deflating the body 215, and the second lumen supports the drawstring 305. The drawstring 305 includes a pull tab 307 (FIG. 9D) at its proximal end and remains exterior of the user.

During removal of the device 210, a pulling action on the pull tab 307 (and thus the drawstring 305) untethers the device from the sutures, e.g., biodegradable (which will remain behind), used to secure the device 210 in position. This drawstring configuration allows the device 210 to be removed less invasively by drawing it through the port and thus the small existing percutaneous hole in the tissue.

The therapeutic delivery device 210 was tested, in triplicate, against well-established MRSA biofilms grown on polyether ether ketone (PEEK) membranes in a modified CDC biofilm reactor. The biofilms were robust and contained $7.07 \pm 2.42 \times 10^7$ CFU/membrane. The devices were loaded with 15 mL of a triple-antibiotic solution in PBS: 2 mg/ml rifampin, 25 mg/mL gentamycin, and 75 mg/ml fosfomycin. The devices and biofilm membranes were submerged in 30 mL of 10% BHI and incubated at 37° C. The biofilms were completely eradicated for all three devices tested within 24 hours.

Figures 10A, 10B:
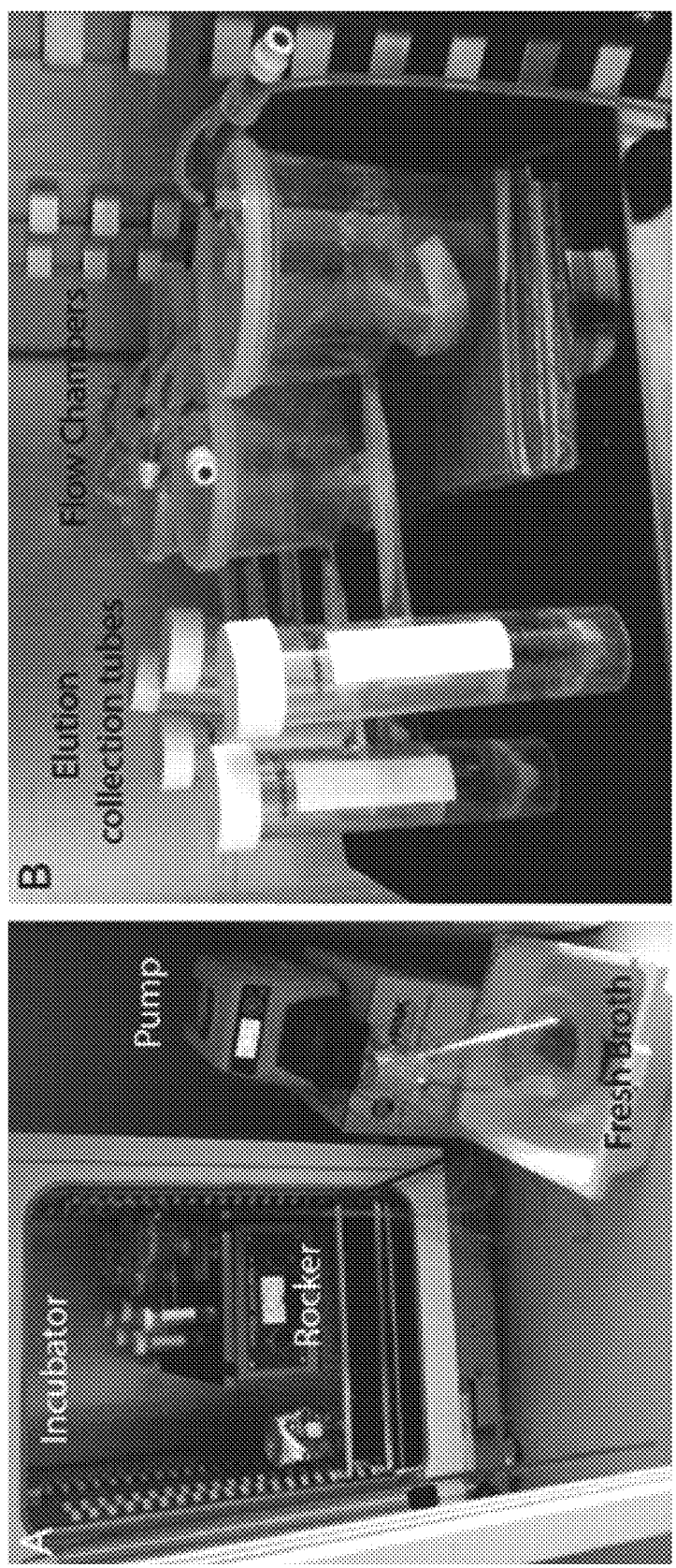
FIG. 10A is a photograph of a first portion of a testing apparatus.
FIG. 10B is a photograph of a second portion of a testing apparatus.
Figure 11A:
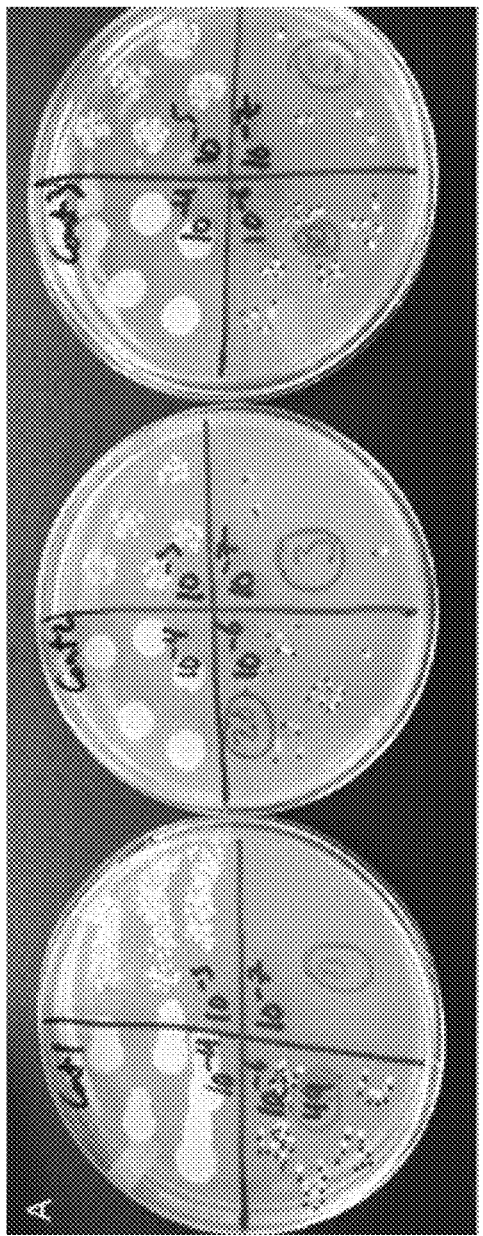
FIG. 11A is a photograph of a set of testing objects.
Figure 11B:
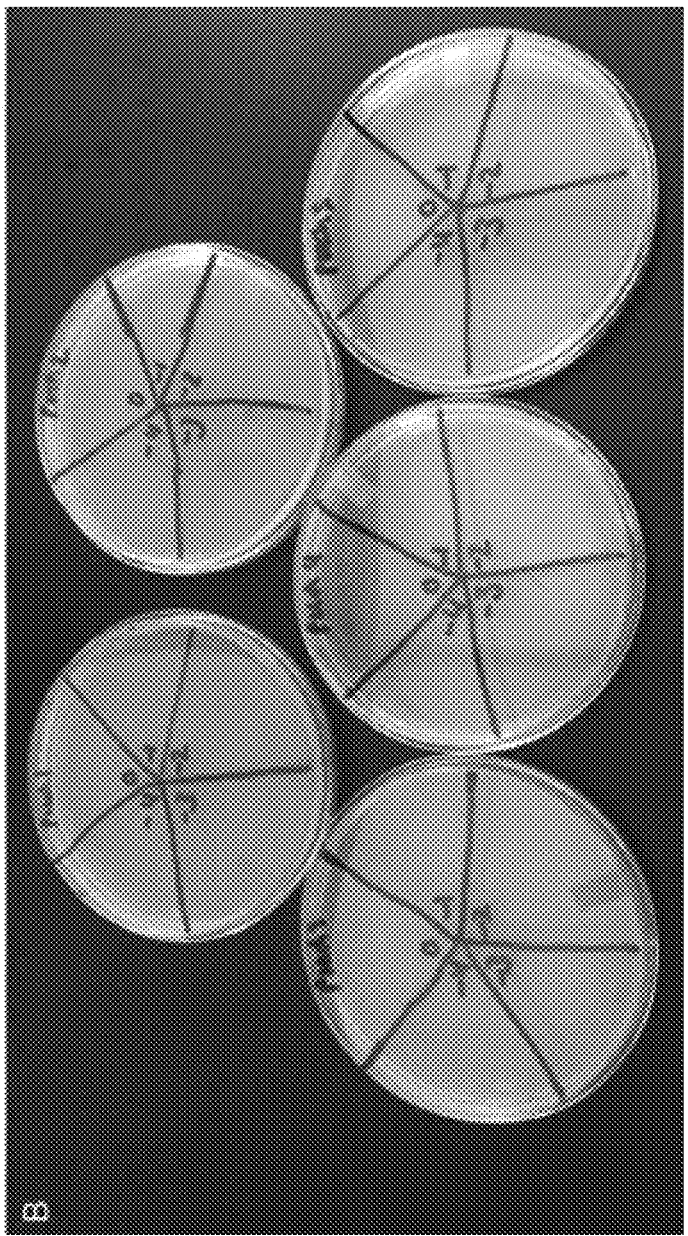
FIG. 11B is a photograph of another set of testing objects.

This in vitro model was then expanded to account for lymphatic flow, which will inevitably clear antibiotics from living tissues, as would be the case if the device were used as intended and implanted in an operation site. The model setup is illustrated in FIGS. 10A-B. Briefly, the devices were loaded with a 15 ml solution of triple-antibiotic and each submerged in 50 ml of 10% BHI in a flow chamber (FIG. 10B). Similarly, MRSA biofilms at $6.60 \pm 2.95 \times 10^8$ CFU/membrane (FIG. 11A), were placed in each flow chamber. A fresh solution of 10% BHI was continually pumped through each cell with an exchange rate of 16% per hour to mimic the clearance rate in human tissues. Within 24 hours, the associated biofilms were completely eradicated for all 5 devices tested (FIG. 11B).

Figures 12A, 12B, 12C:
FIGS. 12A-C is a set of photographs illustrating exemplary use of the therapeutic delivery device of FIG. 6A.
Figure 13:
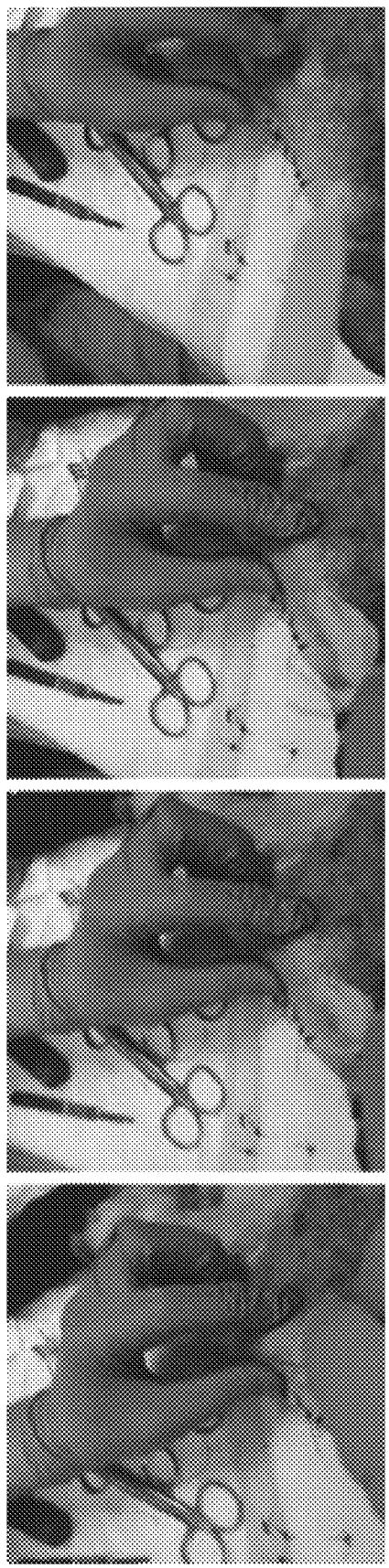
FIG. 13 is a set of photographs illustrating exemplary extraction of the therapeutic delivery device from a test subject.

Referring to FIG. 12, a procedure was performed with the therapeutic delivery device 210 in a sheep carcass. In this procedure, an incision was made in the proximal medial aspect of the sheep tibia. After placement of the orthopedic implants (image A) the inflated/filled device 210 (image B) was anchored to the skin with a suture in each corner (e.g., via the holes 270), thereby ensuring the device 210 sat firmly just above the implant. Then the wound was closed (image C). A bulbous protrusion was created by the inflated percutaneous device 210. The device 210 was easily extracted by cutting the four anchoring sutures, deflating the device 210, and gently sliding it out through the small percutaneous port hole (FIG. 13).

There are multiple benefits associated with the therapeutic delivery device 10. For example, the device 10 can provide local, high dose release of therapeutic agents into the surrounding tissue and fluid of a patient—an important requirement to treat and prevent infection (e.g., biofilm device-related infection, etc.). Another exemplary benefit of the device 10 is the ability to sustain that high dose release of therapeutic agent via the reloadable or refillable design, which may reduce the risk of resistance development. A final exemplary benefit would be the versatility of the device 10. For example, the device 10 has the ability to be loaded with a variety of therapeutic agents other than antimicrobials, including traditional antibiotics, nanotechnologies, or novel antimicrobials that are under development.

Figure 16:
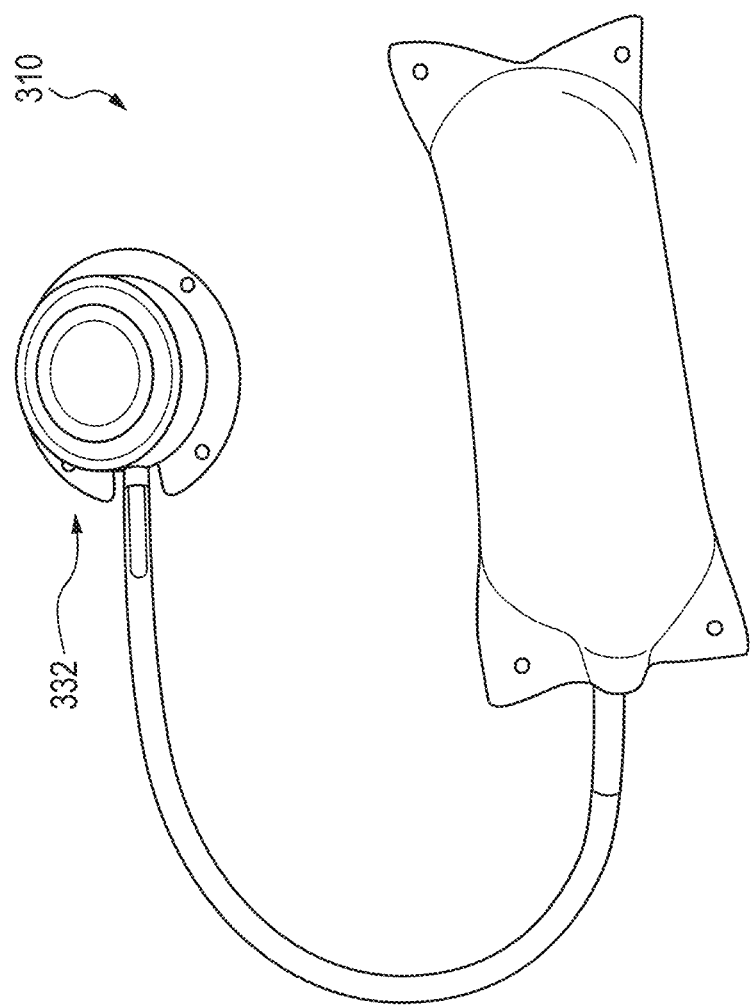
FIG. 16 shows another embodiment of a therapeutic delivery device.

FIG. 16 illustrates a therapeutic delivery device 310 according to another embodiment of the present invention. The device 310 is substantially similar to the devices 10, 110, 210 described above. The features of the device 310 that are substantially the same as the features of the devices 10, 110, 210 are indicated by the same reference numerals as device 10 plus "300." The follow description will focus primarily on the differences between the device 310 and the devices 10, 110, 210. However, it should be noted that features from the device 310 may be used on the devices 10, 110, 210 and vice versa.

The therapeutic delivery device 310 includes a subcutaneous port 332 coupled to the body 315. In this embodiment, the subcutaneous port 332 is placed into the patient beneath subcutaneous tissue and may be accessed, for example, using a needle. This configuration allows for a refilling system in which no portion of the pouch 310 extends percutaneously. This may, for example, reduce the risk of infection proximate the port.

Although the invention has been described in detail with reference to certain preferred embodiments, variations and modifications exist within the scope and spirit of one or more independent aspects of the invention as described.

What is claimed is:

1. A therapeutic delivery device, the device comprising:
an at least semi-rigid housing
a body defining an internal reservoir for holding a therapeutic agent and including a first membrane for release of the therapeutic agent to a surgical site;
a port in fluid communication with the reservoir and being configured such that the reservoir can be refilled via the port; and
the body configured to receive at least one fastener and including a second membrane to deliver the therapeutic agent from the body to the surgical site;
wherein the at least semi-rigid housing includes an upper portion and a lower portion, the lower portion including a first portion and a second portion coupled to the lower portion, wherein the first portion and the second portion swing open to release the body and the first portion is coupled to a first side of the lower portion and the second portion is coupled to a second side of the lower portion.

2. The therapeutic delivery device according to claim 1, wherein the device further comprises a dual lumen, wherein at least one of the dual lumen is in communication with the reservoir.

3. The therapeutic delivery device according to claim 1, wherein the port extends to outside the patient.

4. The therapeutic delivery device according to claim 1, wherein the port is configured to be deployed subdermally such that a user can refill the reservoir via the port.

5. The therapeutic delivery device according to claim 1, wherein the first or second membrane is comprised of a polyurethane film.

6. The therapeutic delivery device according to claim 1, wherein the at least semi-rigid housing includes an upper portion and a lower portion.

7. The therapeutic delivery device according to claim 2, wherein the dual lumen are in relatively close proximity to each other.

8. The therapeutic delivery device according to claim 7, wherein the first or second membrane is a rate determining membrane.

9. A therapeutic delivery device, the device comprising:
an at least semi-rigid housing;
a body defining an internal reservoir for receiving a therapeutic agent and including a first membrane for providing a controlled release of the therapeutic agent to a surgical site;
a port in fluid communication with the reservoir; and
the body configured to receive at least one fastener, the body including a second membrane to deliver the therapeutic agent from the body to the surgical site;
wherein the at least semi-rigid housing includes an upper portion and a lower portion, the lower portion including a first portion and a second portion coupled to the lower portion, wherein the first portion and the second portion swing open to release the body and the first portion is coupled to a first side of the lower portion and the second portion is coupled to a second side of the lower portion.

10. The therapeutic delivery device of claim 9, wherein the first membrane defines a first release rate.

11. The therapeutic delivery device according to claim 9, wherein the port from the body to a surrounding environment.

12. The therapeutic delivery device according to claim 9, wherein the port is configured to be deployed subdermally such that a user can refill the reservoir via the port.

13. The therapeutic delivery device according to claim 9, wherein the first or second membrane is a rate determining membrane.

14. The therapeutic delivery device according to claim 13, wherein the first and second membrane are rate determining membranes.

* * * * *